US009977863B2

(12) United States Patent
Ukai et al.

(10) Patent No.: US 9,977,863 B2
(45) Date of Patent: May 22, 2018

(54) MEDICAL SYSTEM, IMAGE PROCESSING DEVICE, TERMINAL DEVICE, SERVER DEVICE, AND INFORMATION DISPLAY METHOD

(71) Applicant: OLYMPUS CORPORATION, Hachioji-shi, Tokyo (JP)

(72) Inventors: Akihiro Ukai, Tokyo (JP); Masanao Hara, Tokyo (JP); Ken Suzuki, Saitama (JP); Takahiro Narasawa, Tokyo (JP); Katsuhiko Nameta, Tokorozawa (JP); Yasuhiko Okada, Yokohama (JP); Keiichiro Tawara, Tokyo (JP); Yasuhisa Seki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/093,447

(22) Filed: Apr. 7, 2016

(65) Prior Publication Data
US 2016/0217255 A1  Jul. 28, 2016

Related U.S. Application Data

(63) Continuation of application No. PCT/JP2015/067420, filed on Jun. 17, 2015.

(30) Foreign Application Priority Data

Jun. 25, 2014 (JP) .................................. 2014-130019

(51) Int. Cl.
*G06F 19/00* (2018.01)
*G06Q 50/24* (2012.01)

(52) U.S. Cl.
CPC ........... *G06F 19/321* (2013.01); *G06Q 50/24* (2013.01); *G16H 10/65* (2018.01)

(58) Field of Classification Search
CPC ................................. G06T 1/00; G06F 19/321
See application file for complete search history.

(56) References Cited

U.S. PATENT DOCUMENTS 5,568,271 A * 10/1996 Fukuchi ............... G11B 27/002
  348/74
2006/0265252 A1  11/2006 Nishii et al.
(Continued)

FOREIGN PATENT DOCUMENTS

JP     H05-274377 A    10/1993
JP     2006-198042 A    8/2006
(Continued)

OTHER PUBLICATIONS

Aug. 18, 2015 Search Report issued in International Patent Application No. PCT/JP2015/067420.
(Continued)

*Primary Examiner* — Linh Giang Le
(74) *Attorney, Agent, or Firm* — Oliff PLC

(57) ABSTRACT

An image processing device includes: a reading unit that reads an image, image identification information (image ID), and medium identification information (medium ID) from the removable medium; a transmitting unit that transmits, to a server, the image ID and the medium ID that have been read by the reading unit; a receiving unit that receives, from the server, the patient information that corresponds to the image ID and the medium ID that have been transmitted by the transmitting unit, or information indicating no existing corresponding patient information; and a display control unit that displays, on a display device, the image read by the reading unit and the patient information received by the receiving unit, or the image read by the reading unit.

10 Claims, 5 Drawing Sheets

(56) References Cited

U.S. PATENT DOCUMENTS

| | | | | |
|---|---|---|---|---|
| 2012/0238810 A1* | 9/2012 | Kobayashi | ............ | A61B 1/0005 600/109 |
| 2014/0019775 A1* | 1/2014 | Powell | .................... | G06F 21/10 713/193 |

FOREIGN PATENT DOCUMENTS

| | | | |
|---|---|---|---|
| JP | 2006-350998 A | 12/2006 | |
| JP | 2011-257839 A | 12/2011 | |

OTHER PUBLICATIONS

Aug. 18, 2015 Written Opinion issued in International Patent Application No. PCT/JP2015/067420.
Jan. 5, 2016 Decision to Grant issued in Japanese Patent Application No. 2015-552318.

\* cited by examiner

| IMAGE ID | EXAMINATION IMAGE |
|---|---|

FIG. 2

| IMAGE ID | MEMORY ID | PATIENT INFORMATION |

F I G . 3

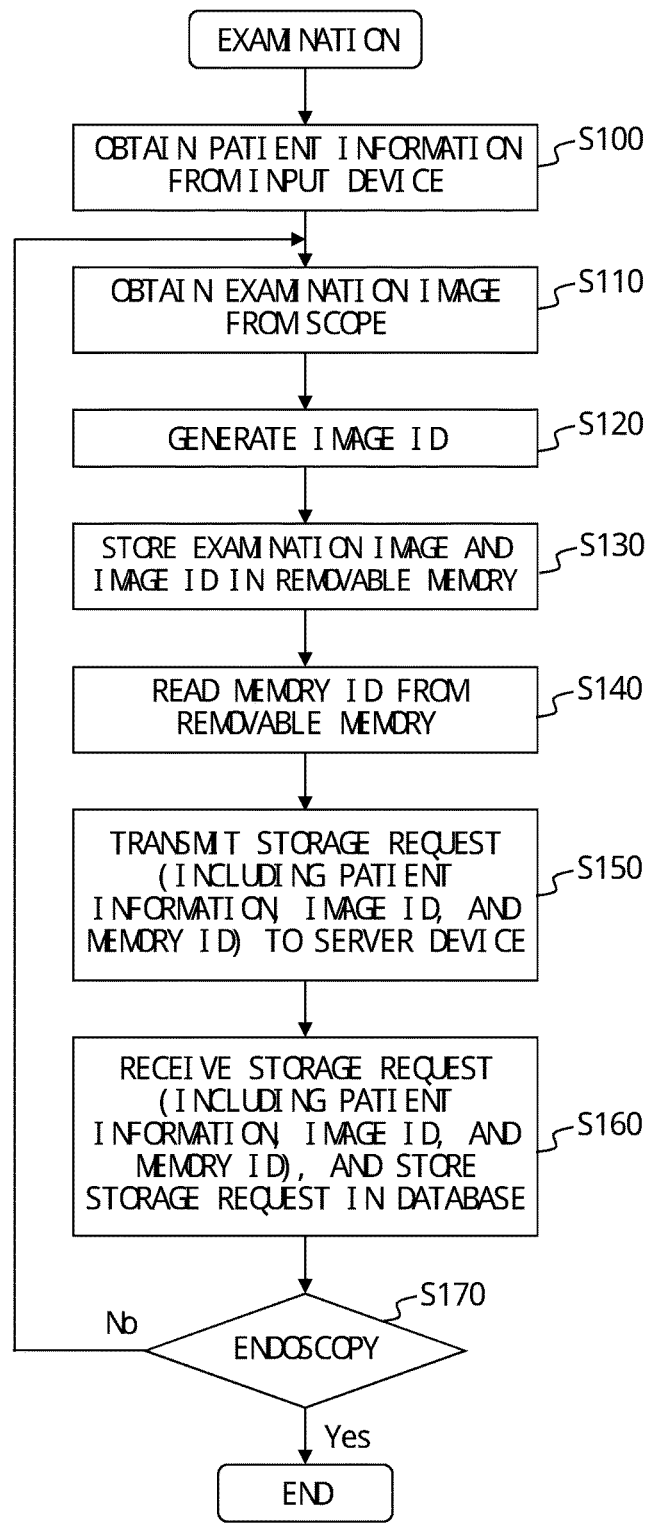
F I G . 4

MEDICAL SYSTEM, IMAGE PROCESSING DEVICE, TERMINAL DEVICE, SERVER DEVICE, AND INFORMATION DISPLAY METHOD

CROSS-REFERENCE TO RELATED APPLICATIONS

This application is based upon and claims the benefit of priority of the prior Japanese Patent Application No. 2014-130019, filed Jun. 25, 2014, the entire contents of which are incorporated herein by reference.

This is a Continuation Application of PCT Application No. PCT/JP2015/067420, filed Jun. 17, 2015, which was not published under PCT Article 21(2) in English.

FIELD

The present invention relates to a medical system used in medical institutions or the like.

BACKGROUND

Conventionally, an endoscope system is used as a medical system used in medical institutes or the like.

The endoscope system includes, for example, an electronic endoscope, a monitor, an endoscope video processor, a terminal device, a removable memory, and the like, and the endoscope system performs the processing below at the time of conducting endoscopy or browsing an examination result. At the time of conducting endoscopy, the endoscope video processor performs processing such as storing of an examination image obtained by the electronic endoscope, together with input patient information (information about a person to be examined), in the removable memory. At the time of browsing an examination result, the endoscope video processor performs processing such as reading of the examination image and the patient information stored in the removable memory and displaying of the examination image and the patient information on the monitor. Alternatively, a terminal device that has been mounted with the removable memory performs processing such as reading of the examination image and the patient information stored in the removable memory and displaying the examination image and the patient information on a display unit.

With respect to the endoscope system, the apparatus below is also known. The apparatus is an endoscopic image recording apparatus including a video endoscope, a monitor, an image control device, an IC memory card, and the like, and the image control device performs processing such as recording an endoscopic image obtained by the video endoscope, together with patient data, in the IC memory card at the time of conducting an examination (see, for example, Japanese Laid-Open Patent Publication No. 5-274377).

In the operation of the endoscope system, the removable memory in which the patient information has been stored together with the examination image is generally managed in such a way that a third party (persons who are not the persons concerned) cannot use the removable memory, for the purpose of the protection of personal information.

SUMMARY

According to an aspect of the present invention, a medical system including an image processing device, a display device, a removable storage medium, and a server device is provided. The image processing device includes: a generating unit that generates identification information of an image that has been input; a writing unit that writes the image and the identification information of the image to the removable storage medium; a first reading unit that reads the identification information of the removable storage medium from the removable storage medium; a first transmitting unit that transmits, to the server device, patient information that has been input, the identification information of the image, and the identification information of the removable storage medium; a second reading unit that reads, from the removable storage medium, the image, the identification information of the image, and the identification information of the removable storage medium; a second transmitting unit that transmits, to the server device, the identification information of the image and the identification information of the removable storage medium that have been read by the second reading unit; a receiving unit that receives, from the server device, the patient information that corresponds to the identification information of the image and the identification information of the removable storage medium that have been transmitted by the second transmitting unit, or information indicating no existing corresponding patient information; and a display control unit that displays, on the display device, the image read by the second reading unit and the patient information received by the receiving unit, or the image read by the second reading unit. The server device includes: a first receiving unit that receives the patient information, the identification information of the image, and the identification information of the removable storage medium that have been transmitted by the first transmitting unit of the image processing device; a storing unit that stores the patient information, the identification information of the image, and the identification information of the removable storage medium that have been received by the first receiving unit; a second receiving unit that receives the identification information of the image and the identification information of the removable storage medium that have been transmitted by the second transmitting unit of the image processing device; a first retrieving unit that retrieves, from the storing unit, the patient information that corresponds to the identification information of the image and the identification information of the removable storage medium that have been received by the second receiving unit; and a first transmitting unit that transmits, to the image processing device, the patient information retrieved by the first retrieving unit or the information indicating no existing corresponding patient information.

According to another aspect of the present invention, an image processing device is provided that includes: a generating unit that generates identification information of an image that has been input; a writing unit that writes the image and the identification information of the image to the removable storage medium; a first reading unit that reads the identification information of the removable storage medium from the removable storage medium; a first transmitting unit that transmits, to a server device, patient information that has been input, the identification information of the image, and the identification information of the removable storage medium; a second reading unit that reads, from the removable storage medium, the image, the identification information of the image, and the identification information of the removable storage medium; a second transmitting unit that transmits, to the server device, the identification information of the image and the identification information of the removable storage medium that have been read by the second reading unit; a receiving unit that receives, from the server device, the patient information that corresponds to the identification information of the image and the identification information of the removable storage medium that have been transmitted by the second transmitting unit, or information indicating no existing corresponding patient information; and a display control unit that displays, on a display device, the image read by the second reading unit and the patient information received by the receiving unit, or the image read by the second reading unit.

According to yet another aspect of the present invention, a terminal device is provided that includes: a reading unit that reads, from a removable storage medium, an image, identification information of the image, and the identification information of the removable storage medium; a transmitting unit that transmits, to a server device, the identification information of the image and the identification information of the removable storage medium that have been read by the reading unit; a receiving unit that receives, from the server device, patient information that corresponds to the identification information of the image and the identification information of the removable storage medium that have been transmitted by the transmitting unit, or information indicating no existing corresponding patient information; and a display unit that displays the image read by the reading unit and the patient information received by the receiving unit, or the image read by the reading unit.

According to yet another aspect of the present invention, a server device is provided that includes: a first receiving unit that receives patient information, identification information of an image, and the identification information of a removable storage medium that have been transmitted by an image processing device or a terminal device; a storing unit that stores the patient information, the identification information of the image, and the identification information of the removable storage medium that have been received by the first receiving unit; a second receiving unit that receives the identification information of the image and the identification information of the removable storage medium that have been transmitted by the image processing device or the terminal device; a retrieving unit that retrieves, from the storing unit, the patient information that corresponds to the identification information of the image and the identification information of the removable storage medium that have been received by the second receiving unit; and a transmitting unit that transmits, to the image processing device or the terminal device, the patient information retrieved by the retrieving unit or information indicating no existing corresponding patient information.

According to yet another aspect of the present invention, an information display method of a medical system including an image processing device, a display device, a removable storage medium, and a server device is provided. The image processing device generates identification information of an image that has been input, writes the image and the identification information of the image to the removable storage medium, reads the identification information of the removable storage medium from the removable storage medium, and transmits, to the server device, patient information that has been input, the identification information of the image, and the identification information of the removable storage medium. The server device receives the patient information, the identification information of the image, and the identification information of the removable storage medium that have been transmitted by the image processing device, and stores the patient information, the identification information of the image, and the identification information of the removable storage medium that have been received in a storing unit. The image processing device reads, from the removable storage medium, the image, the identification information of the image, and the identification information of the removable storage medium, and transmits, to the server device, the identification information of the image and the identification information of the removable storage medium that have been read. The server device receives the identification information of the image and the identification information of the removable storage medium that have been transmitted by the image processing device, retrieves, from the storing unit, the patient information that corresponds to the identification information of the image and the identification information of the removable storage medium that have been received, and transmits, to the image processing device, the patient information that has been retrieved or information indicating no existing corresponding patient information. The image processing device receives the patient information or the information indicating no existing corresponding patient information that has been transmitted by the server device, and displays, on the display device, the image that has been read and the patient information that has been received, or the image that has been read.

BRIEF DESCRIPTION OF DRAWINGS

FIG. 2 illustrates an example of a data structure of image information stored in an image information storage area of a removable memory.

FIG. 3 illustrates an example of a data structure of patient management information stored in a database of a server device.

FIG. 4 is an example of a flowchart illustrating an operation of an endoscope system performed at the time of conducting endoscopy.

DESCRIPTION OF EMBODIMENTS

Embodiments of the present invention are described below with reference to the drawings.

A medical system according to an embodiment of the present invention is an endoscope system used in medical institutions (for example, hospitals).

Figure 1:
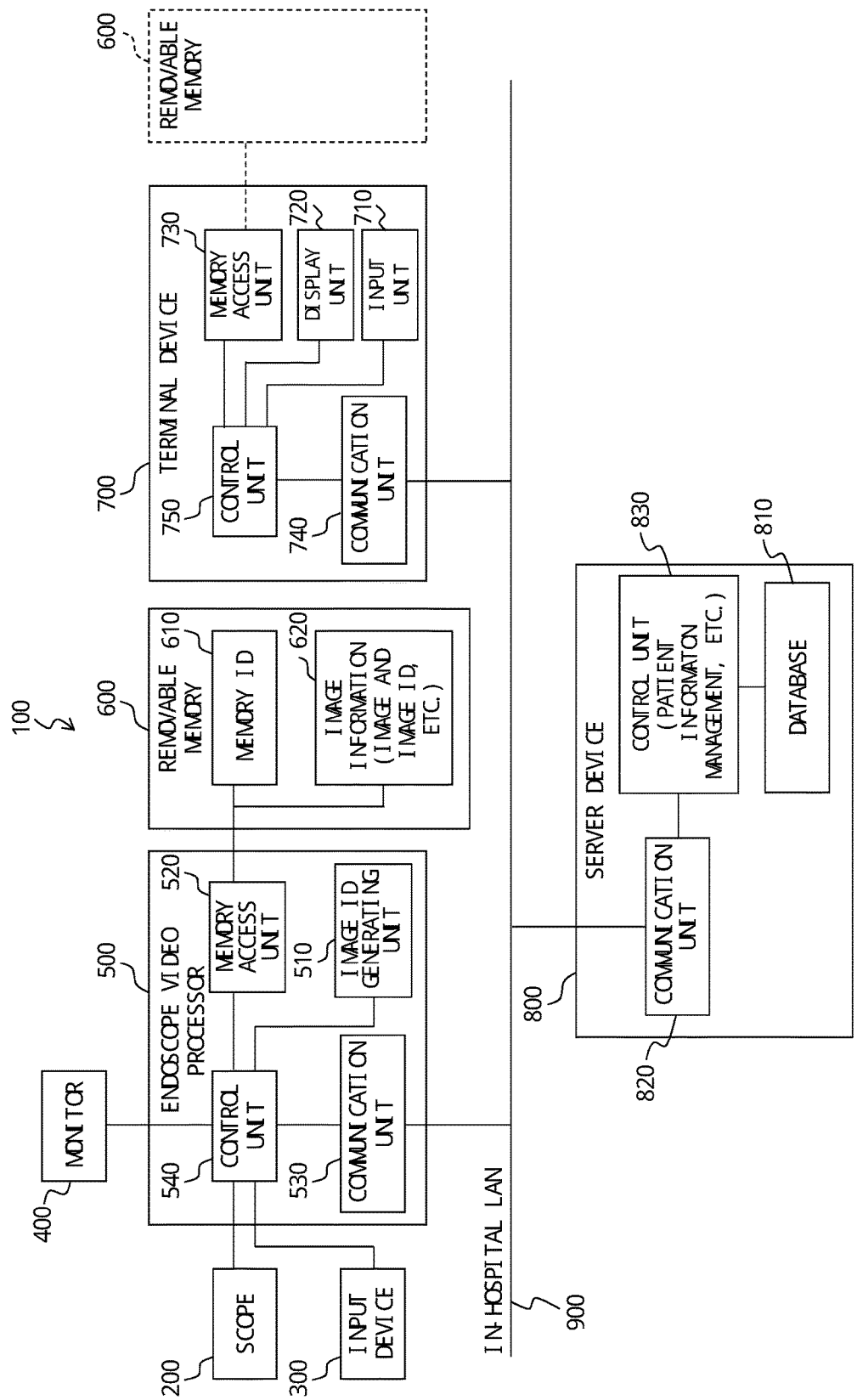
FIG. 1 illustrates an exemplary configuration of an endoscope system that is a medical system according to an embodiment.

FIG. 1 illustrates an exemplary configuration of the endoscope system.

As illustrated in FIG. 1, an endoscope system 100 includes a scope (an electronic endoscope) 200, an input device 300, a monitor 400, an endoscope video processor 500, a removable memory 600, a terminal device 700, a server device 800, and an in-hospital LAN (Local Area Network) 900. The scope 200, the input device 300, and the monitor 400 are connected to the endoscope video processor 500. The removable memory 600 is a memory that can be attached to or detached from the endoscope video processor 500 and the terminal device 700, and FIG. 1 illustrates an example in which the removable memory 600 is mounted onto the endoscope video processor 500. The endoscope video processor 500, the terminal device 700, and the server device 800 are connected to the in-hospital LAN 900.

In the endoscope system 100, the scope 200 images a subject so as to obtain an image (an examination image or an endoscopic image), and outputs the image to the endoscope video processor 500.

Examples of the input device 300 include a keyboard, a mouse, and a touch panel, and the input device 300 receives various inputs (for example, an input of patient information or the like) from a user (for example, a doctor or a nurse), and outputs the various inputs to the endoscope video processor 500.

Examples of the monitor 400 include a liquid crystal display device, and the monitor 400 performs various displays according to video signals output from the endoscope video processor 500.

The endoscope video processor 500 includes an image ID (Identification) generating unit 510, a memory access unit 520, a communication unit 530, and a control unit 540.

The image ID generating unit 510 generates an image ID that is identification information of an image that has been input from the scope 200 to the endoscope video processor 500.

The memory access unit 520 writes and reads information to/from the removable memory 600 mounted onto the endoscope video processor 500. Details are described later, but the memory access unit 520 performs, for example, writing of an image and an image ID to the removable memory 600, reading of a memory ID that is identification information of the removable memory 600 from the removable memory 600, and reading of the image, the image ID, and the memory ID from the removable memory 600.

The communication unit 530 communicates with an external device (for example, the server device 800) that is connected to the in-hospital LAN 900. Details are described later, but the communication unit 530 performs, for example, transmission to the server device 800 of an image ID, a memory ID, and patient information that has been input to the endoscope video processor 500, transmission to the server device 800 of the image ID and the memory ID that have been read by the memory access unit 520, or reception from the server device 800 of patient information that corresponds to the image ID and the memory ID or information indicating no existing corresponding patient information.

The control unit 540 controls the entire operation of the endoscope video processor 500, and also controls the scope 200, the input device 300, and the monitor 400. Details are described later, but the control unit 540 performs, for example, displaying on the monitor 400 of the image read by the memory access unit 520 and the patient information received by the communication unit 530, or the image read by the memory access unit 520.

Figure 2:
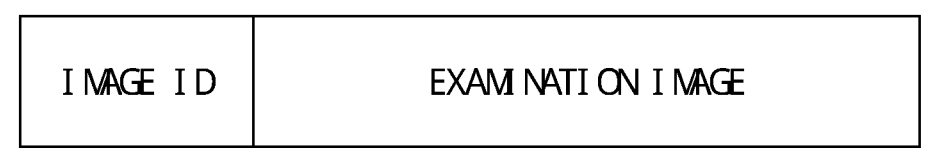

Examples of the removable memory 600 include a removable non-volatile memory such as a USB (Universal Serial Bus) memory, and the removable memory 600 includes a memory ID storage area 610 in which a memory ID that is identification information of the removable memory 600 is stored, and an image information storage area 620 in which image information is stored. The memory ID stored in the memory ID storage area 610 is stored, for example, when the removable memory 600 is shipped from a factory, and in principle, the memory ID cannot be rewritten by a user. The image information stored in the image information storage area 620 has a data structure including an image ID and an image (an examination image) associated with the image ID, as illustrated in FIG. 2, for each of the image IDs.

Examples of the terminal device 700 include a PC (Personal Computer) and a tablet terminal device, and the terminal device 700 includes an input unit 710, a display unit 720, a memory access unit 730, a communication unit 740, and a control unit 750.

Examples of the input unit 710 include a keyboard, a mouse, and a touch panel, and the input unit 710 receives various inputs from a user, and outputs the various inputs to the control unit 750.

Examples of the display unit 720 include a liquid crystal display unit, and the display unit 720 performs various displays according to video signals output from the control unit 750. Details are described later, but the display unit 720 performs, for example, displaying of an image read by the memory access unit 730 and patient information received by the communication unit 740, or the image read by the memory access unit 730.

The memory access unit 730 writes and reads information to/from the removable memory 600 mounted onto the terminal device 700. Details are described later, but the memory access unit 730 performs, for example, reading of the image, the image ID, and the memory ID from the removable memory 600.

The communication unit 740 communicates with an external device (for example, the server device 800) that is connected to the in-hospital LAN 900. Details are described later, but the communication unit 740 performs, for example, transmission to the server device 800 of the image ID and the memory ID read by the memory access unit 730, or reception from the server device 800 of patient information that corresponds to the image ID and the memory ID or information indicating no existing corresponding patient information.

The control unit 750 controls the entire operation of the terminal device 700.

The server device 800 includes a database 810, a communication unit 820, and a control unit 830.

Figure 3:
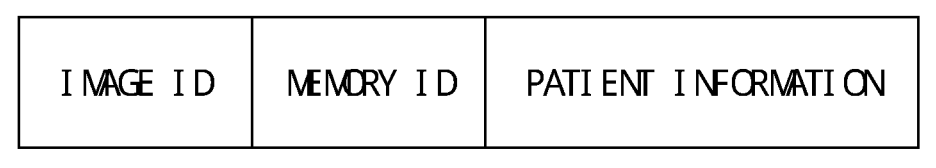

In the database 810, patient management information or the like is stored. The patient management information has a data structure that includes an image ID, and a memory ID and patient information associated with the image ID, as illustrated in FIG. 3, for each of the image IDs. Details are described later, but the image ID, the memory ID, and the patient information in the patient management information stored in the database 810 are received, for example, by the communication unit 820.

The communication unit 820 communicates with an external device (for example, the endoscope video processor 500 or the terminal device 700) that is connected to the in-hospital LAN 900. Details are described later, but the communication unit 820 performs, for example, receiving of the patient information, the image ID, and the memory ID that have been transmitted by the communication unit 530 of the endoscope video processor 500, receiving of the image ID and the memory ID that have been transmitted by the communication unit 530 of the endoscope video processor 500, receiving of the image ID and the memory ID that have been transmitted by the communication unit 740 of the terminal device 700, or transmission to the endoscope video processor 500 or the terminal device 700 of patient information retrieved by the control unit 830 or information indicating no existing corresponding patient information.

The control unit 830 controls the entire operation (including a patient information management operation) of the server device 800. Details are described later, but the control unit 830 performs, for example, retrieval from the database 810 of patient information that corresponds to the image ID and the memory ID received by the communication unit 820.

The in-hospital LAN 900 is configured of a wired LAN and/or a wireless LAN.

In the endoscope system 100, the monitor 400 is an example of a display device. The endoscope video processor 500 is an example of an image processing device. The removable memory 600 is an example of a removable storage medium.

In the endoscope video processor 500, the image ID generating unit 510 is an example of a generating unit that generates identification information of an input image. The memory access unit 520 is an example of a writing unit that writes an image and identification information of the image to a removable storage medium, a first reading unit that reads identification information of the removable storage medium from the removable storage medium, and a second reading unit that reads the image, the identification information of the image, and the identification information of the removable storage medium from the removable storage medium. The communication unit 530 is an example of a first transmitting unit that transmits input patient information, the identification information of the image, and the identification information of the removable storage medium to the server device, a second transmitting unit that transmits, to the server device, the identification information of the image and the identification information of the removable storage medium that have been read by the second reading unit, and a receiving unit that receives, from the server device, patient information that corresponds to the identification information of the image and the identification information of the removable storage medium that have been transmitted by the second transmitting unit, or information indicating no existing corresponding patient information. The control unit 540 is an example of a display control unit that displays the image read by the second reading unit and the patient information received by the receiving unit, or the image read by the second reading unit on a display unit.

In the terminal device 700, the memory access unit 730 is an example of a reading unit that reads the image, the identification information of the image, and the identification information of the removable storage medium from the removable storage medium. The communication unit 740 is an example of a transmitting unit that transmits, to the server device, the identification information of the image and the identification information of the removable storage medium that have been read by the reading unit, and a receiving unit that receives, from the server device, patient information that corresponds to the identification information of the image and the identification information of the removable storage medium that have been transmitted by the transmitting unit, or information indicating no existing corresponding patient information. The display unit 720 is an example of a display unit that displays the image read by the reading unit and the patient information received by the receiving unit, or the image read by the reading unit.

In the server device 800, the communication unit 820 is an example of a first receiving unit that receives the patient information, the identification information of the image, and the identification information of the removable storage medium that have been transmitted by the first transmitting unit of the image processing device, a second receiving unit that receives the identification information of the image and the identification information of the removable storage medium that have been transmitted by the second transmitting unit of the image processing device, a first transmitting unit that transmits, to the image processing device, the patient information retrieved by a first retrieving unit or information indicating no existing corresponding patient information, a third receiving unit that receives the identification information of the image and the identification information of the removable storage medium that have been transmitted by the transmitting unit of the terminal device, and a second transmitting unit that transmits, to the terminal device, patient information retrieved by a second retrieving unit or the information indicating no existing corresponding patient information. The database 810 is an example of a storing unit that stores the patient information, the identification information of the image, and the identification information of the removable storage medium that have been received by the first receiving unit. The control unit 830 is an example of a first retrieving unit that retrieves, from the storing unit, patient information that corresponds to the identification information of the image and the identification information of the removable storage medium that have been received by the second receiving unit, and a second retrieving unit that retrieves, from the storing unit, patient information that corresponds to the identification information of the image and the identification information of the removable storage medium that have been received by the third receiving unit.

In the server device 800, the communication unit 820 is also an example of a first receiving unit that receives the patient information, the identification information of the image, and the identification information of the removable storage medium that have been transmitted by the image processing device or the terminal device, a second receiving unit that receives the identification information of the image and the identification information of the removable storage medium that have been transmitted by the image processing device or the terminal device, and a transmitting unit that transmits, to the image processing device or the terminal device, patient information retrieved by a retrieving unit or information indicating no existing corresponding patient information. The database 810 is an example of a storing unit that stores the patient information, the identification information of the image, and the identification information of the removable storage medium that have been received by the first receiving unit. The control unit 830 is also an example of a retrieving unit that retrieves, from the storing unit, patient information that corresponds to the identification information of the image and the identification information of the removable storage medium that have been received by the second receiving unit.

An operation of the endoscope system 100 is described next.

As an example, operations of the endoscope system 100 performed at the time of conducting endoscopy and at the time of browsing a result of the endoscopy are described here.

FIG. 4 is an example of a flowchart illustrating an operation of the endoscope system 100 performed at the time of conducting endoscopy.

As illustrated in FIG. 4, at the time of conducting endoscopy on a patient that is a person to be examined, the control unit 540 of the endoscope video processor 500 first obtains patient information that has been input by a user via the input device 300 (S100). The patient information is information relating to the patient that is a person to be examined, and the patient information includes personal information of the patient, such as a name, an age, contact information, or a medical history of the patient. In S100, the patient information does not always need to be input via the input device 300, and the patient information may be input, for example, via an external device (for example, the input unit 710 of the terminal device 700) that is connected to the in-hospital LAN 900, and may be obtained by the control unit 540 of the endoscope video processor 500.

Then, the control unit 540 obtains an image (an examination image or an endoscopic image) of the patient that has been imaged by the scope 200 and that has been input from the scope 200 to the endoscope video processor 500 (S110).

The image ID generating unit 510 of the endoscope video processor 500 generates an image ID of the image obtained in S110 (S120).

The memory access unit 520 of the endoscope video processor 500 writes (stores) the image (the examination image) obtained in S110 and the image ID generated in S120 to the image information storage area 620 of the removable memory 600 in accordance with the data structure illustrated in FIG. 2 (S130).

The memory access unit 520 reads a memory ID from the memory ID storage area 610 of the removable memory 600 (S140).

The communication unit 530 of the endoscope video processor 500 transmits, to the server device 800, a storage request to store the patient information obtained in S100, the image ID generated in S120, and the memory ID read in S140 in the database 810 of the server device 800 (S150). The storage request includes the patient information obtained in S100, the image ID generated in S120, and the memory ID read in S140.

The communication unit 820 of the server device 800 receives the storage request transmitted in S150, and the control unit 830 of the server device 800 stores the patient information, the image ID, and the memory ID included in the storage request in the database 810 in accordance with the data structure illustrated in FIG. 3 (S160).

The control unit 540 of the endoscope video processor 500 determines whether endoscopy on the patient that is a person to be examined has been finished (S170). In this determination, as an example, when an instruction to finish endoscopy has been input by a user via the input device 300, the determination result in S170 is Yes. Otherwise, the determination result in S170 is No.

In the determination in S170, when the determination result is No, the process returns to S110, and when the determination result is Yes, this operation is terminated.

As a result of the operation above, at the time of conducting endoscopy, every time the endoscope video processor 500 obtains an image from the scope 200, the image and a corresponding image ID are associated with each other, and are stored in the removable memory 600. In addition, the image ID, a memory ID of the removable memory 600, and patient information are associated with each other, and are stored in the database 810 of the server device 800.

Figure 5:
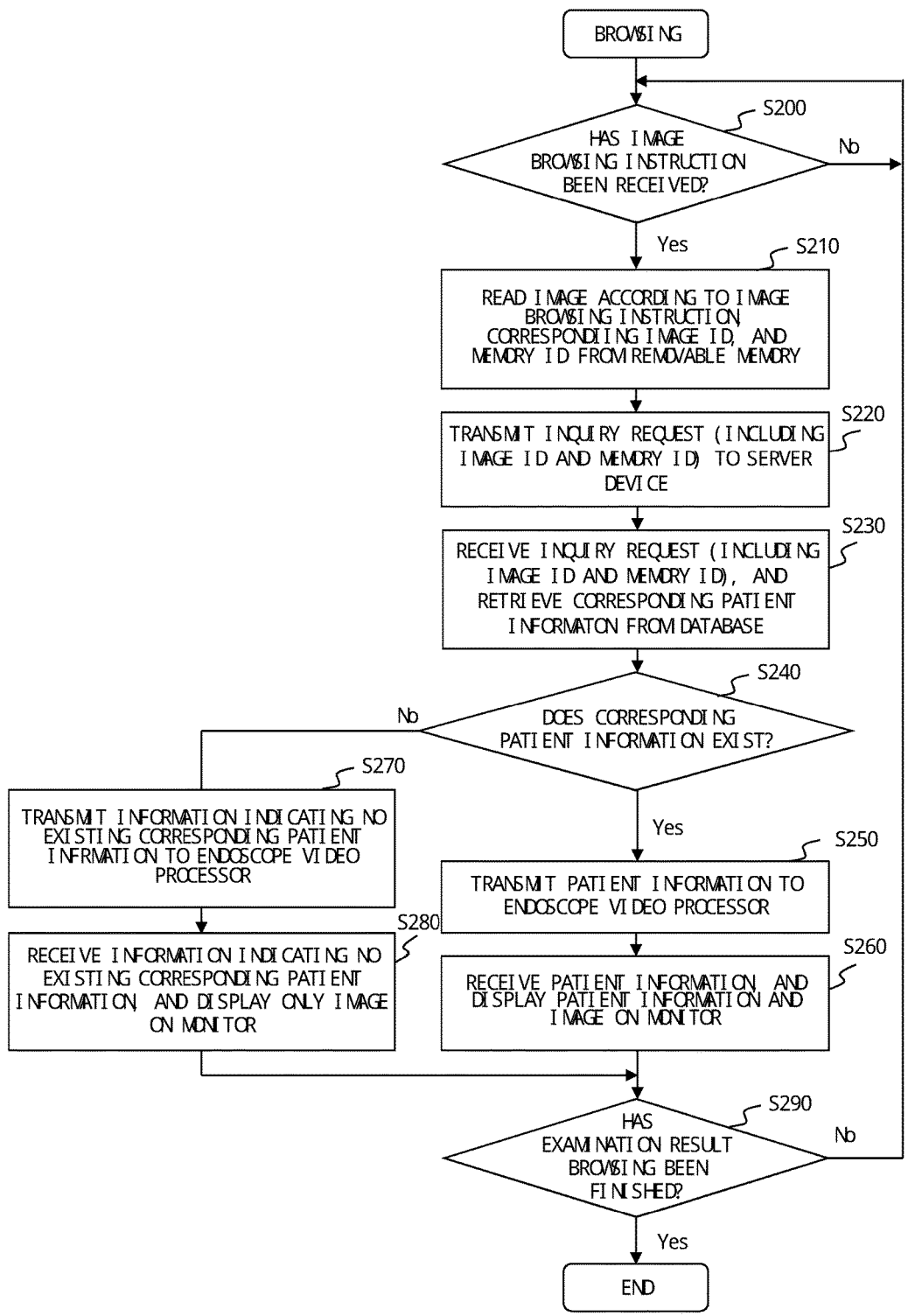
FIG. 5 is an example of a flowchart illustrating an operation of an endoscope system performed at the time of browsing a result of endoscopy.

FIG. 5 is an example of a flowchart illustrating an operation of the endoscope system 100 performed at the time of browsing a result of endoscopy.

As illustrated in FIG. 5, at the time of browsing a result of endoscopy, the control unit 540 of the endoscope video processor 500 determines whether an image browsing instruction input by a user via the input device 300 has been received (S200). The image browsing instruction is an instruction to browse a specific image stored in the image information storage area 620 of the removable memory 600.

When the determination result in S200 is No, this determination is repeated.

When the determination result in S200 is Yes, the memory access unit 520 of the endoscope video processor 500 reads an image according to the image browsing instruction and a corresponding image ID from the image information storage area 620 of the removable memory 600, and also reads a memory ID from the memory ID storage area 610 of the removable memory 600 (S210).

The communication unit 530 of the endoscope video processor 500 transmits, to the server device 800, an inquiry request to inquire about patient information that corresponds to the image read in S210 (the image according to the image browsing instruction) of the server device 800 (S220). The inquiry request includes the image ID and the memory ID that have been read in S210.

The communication unit 820 of the server device 800 receives the inquiry request transmitted in S220, and the control unit 830 of the server device 800 retrieves patient information that corresponds to the image ID and the memory ID included in the inquiry request from the database 810 (S230).

The control unit 830 determines from a result of retrieval in S230 whether patient information that corresponds to the image ID and the memory ID exists (S240).

When the determination result in S240 is Yes, the communication unit 820 transmits, to the endoscope video processor 500, the patient information that corresponds to the image ID and the memory ID as a response to the inquiry request received in S230 (S250).

Following S250, the communication unit 530 of the endoscope video processor 500 receives the patient information transmitted in S250, and the control unit 540 of the endoscope video processor 500 displays the patient information and the image read in S210 on the monitor 400 (S260).

When the determination result in S240 is No, the communication unit 820 of the server device 800 transmits, to the endoscope video processor 500, information indicating no existing corresponding patient information reporting that corresponding patient information does not exist, as a response to the inquiry request received in S230 (S270).

Following S270, the communication unit 530 of the endoscope video processor 500 receives the information indicating no existing corresponding patient information transmitted in S270, and the control unit 540 of the endoscope video processor 500 displays only the image read in S210 on the monitor 400 (S280).

Following S260 or S280, the control unit 540 of the endoscope video processor 500 determines whether browsing of an examination result has been finished (S290). In this determination, as an example, when an instruction to finish browsing an examination result has been input by a user via the input device 300, the determination result in S290 is Yes, and otherwise, the determination result in S290 is No.

In the determination in S290, when the determination result is No, the process returns to S200, and when the determination result is Yes, this operation is terminated.

The operation illustrated in FIG. 5 has been described to be an operation that is performed primarily between the endoscope video processor 500 and the server device 800 under the assumption that the removable memory 600 has been mounted onto the endoscope video processor 500. However, as an example, when the removable memory 600 is removed from the endoscope video processor 500, and is mounted onto the terminal device 700, a similar operation may be performed primarily between the terminal device 700 and the server device 800.

In this case, the operation is performed as described below in accordance with the flow illustrated in FIG. 5.

First, in S200, the control unit 750 of the terminal device 700 determines whether an image browsing instruction input by a user via the input unit 710 has been received. When the determination result is No, this determination is repeated.

When the determination result in S200 is Yes, in S210, the memory access unit 730 of the terminal device 700 reads an image according to the image browsing instruction and a corresponding image ID from the image information storage area 620 of the removable memory 600, and also reads a memory ID from the memory ID storage area 610 of the removable memory 600.

In S220, the communication unit 740 of the terminal device 700 transmits, to the server device 800, an inquiry request to inquire about patient information that corresponds to the image read in S210 (the image according to the image browsing instruction) of the server device 800. The inquiry request includes the image ID and the memory ID read in S210.

In S230, the communication unit 820 of the server device 800 receives the inquiry request transmitted in S220, and the control unit 830 of the server device 800 retrieves patient information that corresponds to the image ID and the memory ID included in the inquiry request from the database 810.

In S240, the control unit 830 determines from a result of retrieval in S230 whether patient information that corresponds to the image ID and the memory ID exists.

When the determination result in S240 is Yes, in S250, the communication unit 820 transmits, to the terminal device 700, the patient information that corresponds to the image ID and the memory ID as a response to the inquiry request received in S230.

In S260, the communication unit 740 of the terminal device 700 receives the patient information transmitted in S250, and the control unit 750 of the terminal device 700 displays the patient information and the image read in S210 on the display unit 720.

When the determination result in S240 is No, in S270, the communication unit 820 of the server device 800 transmits, to the terminal device 700, information indicating no existing corresponding patient information reporting that corresponding patient information does not exist as a response to the inquiry request received in S230.

In S280, the communication unit 740 of the terminal device 700 receives the information indicating no existing corresponding patient information transmitted in S270, and the control unit 750 of the terminal device 700 displays only the image read in S210 on the display unit 720.

Following S260 or S280, in S290, the control unit 750 of the terminal device 700 determines whether browsing of an examination result has been finished. In this determination, as an example, when an instruction to finish browsing of an examination result has been input by a user via the input unit 710 of the terminal device 700, the determination result in S290 is Yes, and otherwise, the determination result in S290 is No.

In the determination in S290, when the determination result is No, the process returns to S200, and when the determination result is Yes, this operation is terminated.

As a result of the operation above, at the time of browsing a result of endoscopy, every time the image browsing instruction is issued, an image according to the image browsing instruction, a corresponding image ID, and a memory ID are read from the removable memory 600, and patient information that corresponds to the image ID and the memory ID is retrieved. When the patient information exists, the patient information and the read image (the image according to the image browsing instruction) are displayed, and when the patient information does not exist, only the read image (the image according to the image browsing instruction) is displayed.

As described above, in the endoscope system 100 according to the present embodiment, patient information is not stored in the removable memory 600, and consequently, the patient information can be protected even when the removable memory 600 passes into the hands of a third party due to unexpected situations such as theft or loss.

Further, in the endoscope system 100 according to the present embodiment, even when image information stored in the removable memory 600 is illegally copied to another removable memory and the other removable memory is used, patient information is not displayed because a memory ID is different. Consequently, patient information can be protected.

In the endoscope system 100 according to the present embodiment, various operations of the endoscope video processor 500, the terminal device 700, and the server device 800 are implemented by software and/or hardware. As an example, when the various operations are implemented by software, or software and hardware, each of the endoscope video processor 500, the terminal device 700, and the server device 800 includes a CPU (Central Processing Unit), a ROM (Read Only Memory), a RAM (Random Access Memory), and the like, and a program stored in the ROM is stored in the RAM, and is executed by the CPU such that the operation of each of the endoscope video processor 500, the terminal device 700, and the server device 800 is implemented. The program may be stored in the RAM, for example, from an external device connected to the in-hospital LAN 900, and may be executed by the CPU. As another example, each of the endoscope video processor 500, the terminal device 700, and the server device 800 may include a medium reading device, and the program may be stored in the RAM from a removable storage medium installed onto the medium reading device and may be executed by the CPU. In this case, as the removable storage medium, various forms of storage media, such as a CD-ROM (Compact Disc Read Only Memory), a flexible disk, an optical disk, a magneto-optical disk, a DVD (Digital Versatile Disc), or a USB memory, can be used.

The medical system according to the present invention is not limited to a system used in endoscopy, such as the endoscope system 100 according to the present embodiment, and of course, the medical system according to the present invention may be configured so as to be applied to a system used in another medical examination.

The embodiment described above gives a specific example of the present invention in order to easily understand the invention, and the present invention is not limited to the embodiment described above. Various variations or modifications of the present invention can be made without departing from the spirit of the present invention specified in the claims.

As described above, according to the present invention, patient information can be protected even when unexpected situations such as theft or loss of a removable memory occur.

What is claimed is:

1. A medical system comprising:
an image processing device,
a display device,
a removable storage medium, and
a server device, wherein:
the image processing device includes a processor and a memory, the processor being programmed to execute instructions, stored on the memory, to:
generate identification information of an image that has been input;
write the image and the identification information of the image to the removable storage medium such that the image and the identification information of the image are linked to an identification information of the removable storage medium;

perform a first reading of reading the identification information of the removable storage medium from the removable storage medium;

perform a first transmitting of transmitting, to the server device, patient information that has been input, the identification information of the image, and the identification information of the removable storage medium linked to the identification information of the image;

perform a second reading of reading, from the removable storage medium, the image, the identification information of the image, and the identification information of the removable storage medium linked to the identification information of the image;

perform a second transmitting of transmitting, to the server device, a patient information inquiry request that includes the identification information of the image and the identification information of the removable storage medium that have been read by the second reading;

in response to the identification information of the image and the identification information of the removable storage medium included in the patient information inquiry request, which are linked to each other, matching the identification information of the image and the identification information of the removable storage medium transmitted to the server device in the first transmitting, receive, from the server device, the patient information that corresponds to the patient information inquiry request that includes the identification information of the image and the identification information of the removable storage medium that have been transmitted, or information indicating no existing corresponding patient information; and display, on the display device, the image read by the second reading and the received patient information, or the image read by the second reading; and the server device includes a storage device and a processor executing instructions, stored on a memory, to:

perform a first receiving of receiving the patient information, the identification information of the image, and the identification information of the removable storage medium that have been transmitted by the first transmitting performed by the image processing device;

store, in the storage device, the patient information, the identification information of the image, and the identification information of the removable storage medium that have been received by the first receiving such that the image and identification information of the image are linked to the identification information of the removable storage medium;

perform a second receiving of receiving the patient information inquiry request that includes the identification information of the image and the identification information of the removable storage medium that have been transmitted by the second transmitting performed by the image processing device;

retrieve, from the storage device, the patient information that corresponds to the identification information of the image and the identification information of the removable storage medium that are included in the patient information inquiry request that has been received by the second receiving;

determine, based on a result of the retrieving, a presence or absence of patient information that corresponds to the identification information of the image and the identification information of the removable storage medium that are included in the patient information inquiry request;

in response to the identification information of the image and the identification information of the removable storage medium matching the identification information of the image and the identification information of the removable storage medium stored in the storing device, transmit, to the image processing device and based on a result of the determining, the retrieved patient information; and in response to the identification information of the image and the identification information of the removable storage medium not matching the identification information of the image and the identification information of the removable storage medium stored in the storing device, transmit, to the image processing device, information indicating a denial of access to patient information.

2. The medical system according to claim 1, further comprising:

a terminal device including display device and a processor programmed to execute instructions, stored in a memory of the terminal device, to:

read, from the removable storage medium, the image, the identification information of the image, and the identification information of the removable storage medium;

transmit, to the server device, the read identification information of the image and the read identification information of the removable storage medium;

receive, from the server device, the patient information that corresponds to the patient information inquiry request that includes the identification information of the image and the identification information of the removable storage medium that have been transmitted, or the information indicating no existing corresponding patient information; and display, on the display device of the terminal device, the read image and the received patient information, or the read image, wherein the processor of the server device further executes instructions to:

perform a third receiving of receiving the patient information inquiry request that includes the identification information of the image and the identification information of the removable storage medium and that has been transmitted by the terminal device;

perform a second retrieving of retrieving, from the storing device, the patient information that corresponds to the identification information of the image and the identification information of the removable storage medium that are included in the patient information inquiry request that has been received by the third receiving;

perform a second determining, based on a result of the second retrieving, a presence or absence of patient information that corresponds to the identification information of the image and the identification information of the removable storage medium that are included in the patient information inquiry request; and perform a second transmitting of transmitting, to the terminal device and based on a result of the second determining, the patient information retrieved by the second retrieving, or the information indicating no existing corresponding patient information.

3. An image processing device comprising:
a processor and a memory, the processor being programmed to execute instructions, stored on the memory, to:
generate identification information of an image that has been input;
write the image and the identification information of the image to a removable storage medium such that the image and the identification information of the image are linked to an identification information of the removable storage medium;
perform a first reading of reading the identification information of the removable storage medium from the removable storage medium;
perform a first transmitting of transmitting, to a server device, patient information that has been input, the identification information of the image, and the identification information of the removable storage medium linked to the identification information of the image;
perform a second reading of reading, from the removable storage medium, the image, the identification information of the image, and the identification information of the removable storage medium linked to the identification information of the image;
perform a second transmitting of transmitting, to the server device, a patient information inquiry request that includes the identification information of the image and the identification information of the removable storage medium that have been read by the second reading;
in response to the identification information of the image and the identification information of the removable storage medium included in the patient information inquiry request, which are linked to each other, matching the identification information of the image and the identification information of the removable storage medium transmitted to the server device in the first transmitting, receive, from the server device, the patient information that corresponds to the patient information inquiry request that includes the identification information of the image and the identification information of the removable storage medium that have been transmitted, or information indicating no existing corresponding patient information; and
display, on a display device, the image read by the second reading and the received patient information, or the image read by the second reading.

4. The image processing device according to claim 3, wherein when the information indicating no existing corresponding patient information is received, the image read by the second reading is displayed on the display device.

5. A terminal device comprising:
a display device and a processor, the processor being programmed to execute instructions, stored on a memory, to:
read, from a removable storage medium, an image, identification information of the image, and identification information of the removable storage wherein the image and the identification information of the image are linked to the identification information of the removable storage medium;
transmit, to a server device, a patient information inquiry request that includes the read identification information of the image and the read identification information of the removable storage medium;
in response to the identification information of the image and the identification information of the removable storage medium included in the patient information inquiry request, which are linked to each other, matching the identification information of the image and the identification information of the removable storage medium transmitted to the server device in the first transmitting, receive, from the server device, patient information that corresponds to the patient information inquiry request that includes the identification information of the image and the identification information of the removable storage medium that have been transmitted, or information indicating no existing corresponding patient information; and
display, on the display device, the read image and the received patient information, or the read image.

6. The terminal device according to claim 5, wherein when the information indicating no existing corresponding patient information is received, the processor displays the read image on the display device.

7. A server device comprising:
a storage device and a processor, the processor being programmed to execute instructions, stored on a memory, to:
perform a first receiving of receiving patient information, identification information of an image, and identification information of a removable storage medium that have been transmitted by an image processing device or a terminal device;
store, in the storage device, the patient information, the identification information of the image, and the identification information of the removable storage medium that have been received by the first receiving such that the image and identification information of the image are linked to the identification information of the removable storage medium;
perform a second receiving of receiving the patient information inquiry request that includes the identification information of the image and the identification information of the removable storage medium that have been transmitted by the image processing device or the terminal device;
retrieve, from the storing device, the patient information that corresponds to the identification information of the image and the identification information of the removable storage medium that are included in the patient information inquiry request that has been received by the second receiving;
determine, based on a result of the retrieving, a presence or absence of patient information that corresponds to the identification information of the image and the identification information of the removable storage medium that are included in the patient information inquiry request;
in response to the identification information of the image and the identification information of the removable storage medium matching the identification information of the image and the identification information of the removable storage medium stored in the storing device, transmit, to the image processing device or the terminal device and based on a result of the determining, the retrieved patient information; and in response to the identification information of the image and the identification information of the removable storage medium not matching the identification information of the image and the identification information of the removable storage medium stored in the storing device, transmit, to the image processing device, information indicating a denial of access to patient information.

8. The server device according to claim 7, wherein when the result of the determining indicates that the patient information that corresponds to the identification information of the image and the identification information of the removable storage medium that are included in the patient information inquiry request is not present, the information indicating no existing corresponding patient information is transmitted to the image processing device or the terminal device.

9. An information display method of a medical system including an image processing device, a display device, a removable storage medium, and a server device, wherein the image processing device performs:
generating identification information of an image that has been input;
writing the image and the identification information of the image to the removable storage medium such that the image and the identification information of the image are linked to an identification information of the removable storage medium;
reading the identification information of the removable storage medium from the removable storage medium; and
transmitting, to the server device, patient information that has been input, the identification information of the image, and the identification information of the removable storage medium linked to the identification information of the image, the server device performs:
receiving the patient information, the identification information of the image, and the identification information of the removable storage medium that have been transmitted by the image processing device; and
storing the patient information, the identification information of the image, and the identification information of the removable storage medium that have been received in a storage device of the server such that the image and identification information of the image are linked to the identification information of the removable storage medium;

the image processing device performs:
reading, from the removable storage medium, the image, the identification information of the image, and the identification information of the removable storage medium; and
transmitting, to the server device, a patient information inquiry request that includes the identification information of the image and the identification information of the removable storage medium that have been read, the server device performs:
receiving the patient information inquiry request that includes the identification information of the image and the identification information of the removable storage medium and that has been transmitted by the image processing device;
retrieving, from the storage device, the patient information that corresponds to the identification information of the image and the identification information of the removable storage medium that are included in the patient information inquiry request;
determining, based on a result of the retrieving, a presence or absence of patient information that corresponds to the identification information of the image and the identification information of the removable storage medium that are included in the patient information inquiry request;
in response to the identification information of the image and the identification information of the removable storage medium matching the identification information of the image and the identification information of the removable storage medium stored in the storing device, transmitting, to the image processing device and based on a result of the determining, the patient information that has been retrieved or information indicating no existing corresponding patient information; and
in response to the identification information of the image and the identification information of the removable storage medium not matching the identification information of the image and the identification information of the removable storage medium stored in the storing device, transmit, to the image processing device, information indicating a denial of access to patient information, and the image processing device performs:
in response to the identification information of the image and the identification information of the removable storage medium included in the patient information inquiry request, which are linked to each other, matching the identification information of the image and the identification information of the removable storage medium transmitted to the server device in the first transmitting, receiving the patient information or the information indicating no existing corresponding patient information that has been transmitted by the server device; and
displaying, on the display device, the image that has been read and the patient information that has been received, or the image that has been read.

10. The information display method according to claim 9, wherein:
the medical system further includes a terminal device that performs:
reading, from the removable storage medium, the image, the identification information of the image, and the identification information of the removable storage medium; and
transmitting, to the server device, a patient information inquiry request that includes the identification information of the image and the identification information of the removable storage medium that have been read, the server device performs:
receiving the patient information inquiry request that includes the identification information of the image and the identification information of the removable storage medium that have been transmitted by the terminal device;

retrieving, from the storing device, the patient information that corresponds to the identification information of the image and the identification information of the removable storage medium that are included in the patient information inquiry request;

determining, based on a result of the retrieving, a presence or absence of patient information that corresponds to the identification information of the image and the identification information of the removable storage medium that are included in the patient information inquiry request; and transmitting, to the terminal device and based on a result of the determining, the patient information that has been retrieved or the information indicating no existing corresponding patient information, and the terminal device performs:

receiving the patient information or the information indicating no existing corresponding patient information that has been transmitted by the server device; and displaying the image that has been read and the patient information that has been received, or the image that has been read.

\* \* \* \* \*